(12) United States Patent
Haiberger (10) Patent No.: US 11,596,333 B2
(45) Date of Patent: Mar. 7, 2023

(54) OPTOELECTRONIC SENSOR MODULE AND METHOD FOR PRODUCING AN OPTOELECTRONIC SENSOR MODULE

(71) Applicant: OSRAM Opto Semiconductors GmbH, Regensburg (DE)

(72) Inventor: Luca Haiberger, Regensburg (DE)

(73) Assignee: OSRAM OLED GMBH, Regensburg (DE)

(*) Notice: Subject to any disclaimer, the term of this patent is extended or adjusted under 35 U.S.C. 154(b) by 594 days.

(21) Appl. No.: 16/604,083

(22) PCT Filed: May 3, 2018

(86) PCT No.: PCT/EP2018/061355
§ 371 (c)(1),
(2) Date: Oct. 9, 2019

(87) PCT Pub. No.: WO2018/206391
PCT Pub. Date: Nov. 15, 2018

(65) Prior Publication Data
US 2020/0129104 A1    Apr. 30, 2020

(30) Foreign Application Priority Data
May 11, 2017  (DE) .......................... 102017110216.7

(51) Int. Cl.
*A61B 5/1455*    (2006.01)
*A61B 5/00*      (2006.01)
*H01L 25/16*     (2023.01)

(52) U.S. Cl.
CPC ............ *A61B 5/14552* (2013.01); *A61B 5/72* (2013.01); *H01L 25/167* (2013.01)

(58) Field of Classification Search
CPC .............. A61B 5/1455; A61B 5/14552; A61B 2562/12; H01L 25/167
See application file for complete search history.

(56) References Cited

U.S. PATENT DOCUMENTS

| 7,187,961 B2* | 3/2007 | Yamashita | ......... A61B 5/02055 600/310 |
| 8,369,913 B2* | 2/2013 | Nomoto | ............. A61B 5/14552 600/323 |

(Continued)

FOREIGN PATENT DOCUMENTS

| CN | 105307559 A | 2/2016 |
| CN | 105793727 A | 7/2016 |

(Continued)

OTHER PUBLICATIONS

"Light is Wearable Health Monitoring and Fitness Tracking," OSRAM Opto Semiconductors, Light is OSRAM, www.ostram-os.com, 2016, 6 pages.

*Primary Examiner* — Eric F Winakur
(74) *Attorney, Agent, or Firm* — Slater Matsil, LLP (57) ABSTRACT

An optoelectronic sensor module and a method for producing an optoelectronic sensor module are disclosed. In an embodiment an optoelectronic sensor module includes a first semiconductor transmitter chip configured to emit radiation of a first wavelength, a second semiconductor transmitter chip configured to emit radiation of a second wavelength different from the first wavelength, a semiconductor detector chip configured to detect the radiation of the first and second wavelengths, and a first potting body being opaque to the radiation of the first and the second wavelength, wherein the first potting body directly covers side surfaces of the chips and mechanically connects the chips located in a common plane to one another, wherein a distance between the chips is less than or equal to twice an average diagonal length of the chips, and wherein the sensor module is adapted to rest against a body part to be examined.

17 Claims, 9 Drawing Sheets

(56) References Cited

U.S. PATENT DOCUMENTS

| | | |
|---|---|---|
| 9,684,074 B2 | 6/2017 | Schrank et al. |
| 10,219,709 B2 * | 3/2019 | Basu ................. A61B 5/14552 |
| 11,504,035 B2 | 11/2022 | Kintz et al. |
| 2016/0011111 A1 | 1/2016 | Stoll et al. |
| 2016/0029911 A1 | 2/2016 | Lee |
| 2016/0073954 A1 | 3/2016 | Meitav |
| 2016/0190380 A1 | 6/2016 | Luan |
| 2017/0325729 A1 | 11/2017 | Halbritter et al. |

FOREIGN PATENT DOCUMENTS

| | | |
|---|---|---|
| DE | 102013223069 A | 5/2015 |
| DE | 102014117879 A1 | 6/2016 |
| EP | 1491135 A2 | 12/2004 |
| WO | 2015071310 A1 | 5/2015 |
| WO | 2017068149 A1 | 4/2017 |

* cited by examiner

OPTOELECTRONIC SENSOR MODULE AND METHOD FOR PRODUCING AN OPTOELECTRONIC SENSOR MODULE

This patent application is a national phase filing under section 371 of PCT/EP2018/061355, filed May 3, 2018, which claims the priority of German patent application 102017110216.7, filed May 11, 2017, each of which is incorporated herein by reference in its entirety.

TECHNICAL FIELD

An optoelectronic sensor module is specified. In addition, a process for the production of such a sensor module is specified.

SUMMARY OF THE INVENTION

Embodiments provide a sensor module that requires little space.

According to at least one embodiment, the optoelectronic sensor module comprises one or more first semiconductor transmitter chips. The at least one first semiconductor transmitter chip is designed to emit radiation of a first wavelength. For example, the first wavelength is in the near-infrared spectral range, for instance around 940 nm.

According to at least one embodiment, the sensor module comprises one or more second semiconductor transmitter chips. The at least one second semiconductor transmitter chip is designed to emit radiation of a second wavelength. The second wavelength is different from the first wavelength. In particular, the second wavelength lies in the red spectral range, for example, around 660 nm.

According to at least one embodiment, the sensor module comprises one or more third semiconductor transmitter chips for emitting radiation of a third wavelength different from the first and second wavelengths. In particular, at least one third semiconductor transmitter chip is designed to emit green light, for example, with a wavelength of maximum intensity around 535 nm.

According to at least one embodiment, the sensor module comprises one or more semiconductor detector chips, in particular exactly one semiconductor detector chip. The at least one semiconductor detector chip is designed to detect the radiation of the first, second and optionally the third wavelength. The semiconductor detector chip can have several pixels or be single-channel. It is possible that the semiconductor transmitter chips and/or the semiconductor detector chip are operated and/or read out in pulsed mode. This means that the radiation of the various wavelengths can be emitted and detected using a time-division multiplex method to enable the use of a single-channel semiconductor detector chip.

According to at least one embodiment, the sensor module has a potting body. The potting body is preferably opaque to the radiation emitted by the semiconductor transmitter chips. The potting body can be designed to be reflective, especially diffuse reflective, or absorbent. The potting body is in particular made of a plastic material such as an epoxy or an epoxy hybrid material to which a coloring agent such as carbon black may be added. Thus the potting body may appear black or also white or colored.

According to at least one embodiment, the potting body directly covers side surfaces of the semiconductor transmitter chips and the at least one semiconductor detector chip. The side surfaces may be completely or predominantly covered by the potting body, i.e., at least 50% or 70% or 85% of the side surfaces may be directly covered by the potting body. The side surfaces extend transversely, in particular perpendicular to radiation-emitting and radiation-detecting main sides of the semiconductor transmitter chips and the at least one semiconductor detector chip.

According to at least one embodiment, the semiconductor transmitter chips and the at least one semiconductor detector chip are located in a common plane. This means that the semiconductor transmitter chips and at least one semiconductor detector chip are located next to each other, preferably without overlapping, when viewed from above.

In the following, semiconductor transmitter chips together with the at least one semiconductor detector chip are referred to simply as chips.

According to at least one embodiment, the chips are mechanically connected to each other by the potting body. It is possible that the composite of the potting body and the chips is mechanically self-supporting and/or represents the mechanically stabilizing component of the sensor module.

According to at least one embodiment, the chips are arranged close to each other in the potting body and have only a small distance to each other. This is made possible by the integration of the chips in the radiation-opaque potting body. In particular, the distance between the chips is at most twice the average diagonal length of the chips. The preferred distance between the chips is not more than the mean diagonal length or not more than 75% or 50% or 25% of the mean diagonal length. The mean diagonal length is determined across all chips, especially when viewed from above.

According to at least one embodiment, the sensor module is designed to attach to a body part to be examined. This means in particular that the distance between the chips and the body part to be examined is only small. It is possible that a signal transfer from the semiconductor transmitter chips to the at least one semiconductor detector chip occurs only via the body part to be examined. For example, on an optical path which is intended and extends from the semiconductor transmitter chips to at least one semiconductor detector chip, there is no free beam path for the radiation of the various wavelengths. The radiation then runs completely or predominantly, for example, to a path proportion of at least 90% or 95%, in condensed matter and not in gases or in an evacuated area. The body part is, for example, a wrist or a finger. In particular, the body part includes human skin, on which the sensor module preferably rests directly.

In at least one embodiment, the optoelectronic sensor module comprises a first semiconductor transmitter chip for emitting radiation of a first wavelength and a second semiconductor transmitter chip for emitting radiation of a second wavelength different from the first wavelength. A semiconductor detector chip is designed to detect the radiation of the first and second wavelengths. The chips, i.e., the semiconductor transmitter chips and the at least one semiconductor detector chip together, are located in a common plane and are mechanically connected to each other by a potting body which is opaque to the radiation of the first and second wavelength, the potting body extending directly onto the side surfaces of the chips. A distance between the chips is less than or equal to twice the average diagonal length of the chips. The sensor module is designed to rest against a part of a body to be examined, especially directly.

Such an optoelectronic sensor module makes it possible to realize a miniaturized module for the determination of pulse frequency and oxygen saturation in the blood. Such a sensor module is also known as a monitor for biological functions or BioMon for short. In particular, the use of the radiation-opaque potting body allows for a space-saving arrangement of the chips on the one hand, while at the same time there is little or no optical crosstalk between the chips.

Semiconductor transmitter chips are preferably LEDs that can be designed as flip chips. The semiconductor detector chip, such as a photodiode, which functions as the actual sensor, is encapsulated in a preferably light-absorbing material, also referred to as molding.

In molding, emission surfaces, detection surfaces and contact surfaces of the chips are preferentially protected, for example, by foils in foil-assisted injection molding or transfer molding, also known as foil assisted molding.

With the sensor module described here, a compact arrangement can be achieved, also made possible by the integration of optics. Due to the radiation-opaque potting body, the chips can be placed close to each other. Optical crosstalk through translucent channels, such as adhesive joints, can be reduced or avoided.

According to at least one embodiment, the sensor module comprises one or more optics. Preferably several optics are present, which are clearly assigned to each of the chips. This means that there can be a 1:1 assignment between the optics and the chips. Neighboring optics preferably do not touch each other.

According to at least one embodiment, at least one of the optics or some of the optics or all of the optics is a multi-lens array or MLA for short. Such optics are more space-saving than Fresnel lenses, for example. Thus, the use of such optics can further reduce the space requirement of the sensor module.

According to at least one embodiment, the side surfaces of the optics are directly covered by a further potting body which is opaque to the respective radiation. These side surfaces are completely or predominantly covered, in particular at least 60% or 75% or 90%, directly or indirectly by the further potting body. The side surfaces are aligned in particular transversely, especially vertically, to the radiation entry surfaces and radiation exit surfaces of the optics.

According to at least one embodiment, the optics are mechanically integrated into the further potting body. The optics can be located in a common plane that is preferably parallel to the plane of the chips. The further potting body can be based on the same material as the potting body in which the chips are inserted, for example, an epoxy with a dye. Alternatively, the potting body and the further potting body are made of different materials.

According to at least one embodiment, at least one of the optics or all of the optics has an optical axis oriented obliquely to the associated chip. In this case it is possible that a main beam axis or optical axis of the associated chip is changed by the associated optics. In particular, the optical axes of the semiconductor transmitter chips are inclined towards the optical axis of the semiconductor detector chip, so that the optical axes of the chips may intersect or at least approach each other.

According to at least one embodiment, a distance between the chips and a light exit surface of the respective associated optics is not more than 150% or 100% or 50% or 25% of the mean diagonal length of the chips. In other words, the light exit surface of the optics and/or sensor module is close to the chips. In other words, the sensor module is then flat.

According to at least one embodiment, the first wavelength is 940 nm, the second wavelength 660 nm and the third wavelength 535 nm. The mentioned wavelengths refer to a wavelength of maximum intensity. The values given apply preferably with a tolerance of not more than 15 nm or 10 nm or 5 nm.

The sensor module is set up for pulse oximetry according to at least one embodiment. This means that the sensor module can be used to measure both pulse and oxygen saturation in the blood.

It is possible that the sensor module comprises a control unit, an evaluation unit and/or a driver unit in addition to the chips. Such an additional electronic unit is formed, for example, by an integrated circuit such as a user-specific integrated circuit (ASIC). Alternatively, it is possible that such a unit for reading out and/or controlling the chips is located outside the sensor module and that the sensor module, for example, is electrically connected to such a unit or attached to such a unit, for example, soldered on.

Further embodiments provide a method for producing an optoelectronic sensor module. The method is preferably used to produce a sensor module, as specified in connection with one or more of the above-mentioned designs. Features of the process are therefore also disclosed for the sensor module and vice versa.

In at least one embodiment, the method comprises the following steps, preferably in the order given:
providing the chips,
potting the chips so that the potting body is formed, and
applying the optics to the potting body with the chips.

According to at least one embodiment, the optics are glued onto the potting body. This bonding is preferred before the further potting body is produced. When creating the further potting body, the side surfaces of the optics are preferably directly and/or completely covered by a material of the further potting body. It is possible that the adhesive for the optics is limited to an area where the optics are applied. Alternatively, it is possible to apply the adhesive over the entire surface.

According to at least one embodiment, the further potting body is formed directly onto a main side of the potting body when it is produced. This means that between the potting body and the further potting body there is preferably no additional connecting means or an additional connecting means is only in small areas, so that an additional connecting means does not contribute or does not significantly contribute to the adhesion between the further potting body and the potting body.

According to at least one embodiment, the further potting body is produced before the optics are applied to the potting body. This means that the optics are integrated into the further potting body in a previous process step and encapsulated by the further potting body. The further potting body can also be produced with a foil-assisted injection molding or transfer molding.

According to at least one embodiment, the finished further potting body with the integrated optics is attached to the potting body with the chips, for example, glued on, in particular glued on over the entire surface. In this case, there may be a connecting means in the form of an adhesive between the further potting body and the potting body.

The adhesive for attaching the optics or the further potting body to the potting body is preferably transmissive to radiation. In particular, the radiation generated in the semiconductor transmitter chips can pass unhindered or almost unhindered through the adhesive layer. The adhesive layer preferably has only a small thickness, for example, a maximum of 5 μm or 2 μm. A thickness of the adhesive layer is alternatively or additionally not more than 20% or 10% or 5% or 2% of the distance or mean distance between the chips.

In order to avoid optical coupling between the chips via the adhesive layer, the adhesive layer may exhibit comparatively low absorption of the radiation generated by the semiconductor transmitter chips. Since the thickness of the adhesive layer is considerably less than a longitudinal expansion of the adhesive layer between the chips, the adhesive layer is then transmissive to the radiation in the direction perpendicular to the light exit side and substantially opaque in the direction transverse to the light exit side.

According to at least one embodiment, a detection side of the potting body is opposite a mounting side of the sensor module. Electrical conducting paths can be generated on the detection side before the optics are attached or after they have been attached. The chips can be electrically connected to each other via the electrical conductor tracks, at least on the detection side.

According to at least one embodiment, the detection side, in particular the entire detection side including the conductor tracks, is covered with an intermediate layer after production of the conductor tracks. The intermediate layer is preferably continuous and uninterrupted. Furthermore, the intermediate layer is preferably transparent and/or transmissive to radiation, so that the intermediate layer is transparent to the radiation emitted by the semiconductor transmitter chips.

According to at least one embodiment, the intermediate layer previously applied over the entire surface is structured. This structuring partially or completely exposes the conductor tracks. The intermediate layer remains only in partial areas on the detection side of the potting body.

According to at least one embodiment, the optics are applied to the areas of the intermediate layer remaining after structuring. This can be done by gluing. Alternatively, the intermediate layer itself serves as an adhesive layer.

In addition, it is possible that the intermediate layer is not applied over the entire surface and then structured, but is only applied locally, for example, via a printing process.

According to at least one embodiment, after the optics have been applied to the intermediate layer, the further potting body is produced. The further potting body can thus be in direct contact with the side surfaces of the optics, with the side surfaces of the intermediate layer and/or with the potting body in which the chips are integrated.

According to at least one embodiment, the potting body with the integrated chips is applied to a carrier or the potting body is produced on a carrier on which the chips were previously applied. The carrier can be a permanent carrier of the sensor module. The support may be made of an electrically insulating base material such as glass or ceramic or plastic. It is also possible that the carrier is based on a semiconductor material and, for example, forms a unit for driving and/or reading out the chips. The carrier preferably comprises several electrical vias produced in or on the base material or semiconductor material.

According to at least one embodiment, all electrical contact surfaces of the sensor module are located on a side of the carrier facing away from the chips. This means that the sensor module can only be connected electrically via the carrier and preferably also mechanically.

According to at least one embodiment, the sensor module can be surface mounted. This means that the sensor module can be mounted using Surface Mount Technology (SMT).

According to at least one embodiment, the conductor tracks on the detection side are electrically connected to the vias and/or to electrical contact surfaces. The vias preferably run completely through the carrier and/or the potting body and/or the further potting body, in the direction transverse or perpendicular to the detection side. The electrical connection of the conductor tracks to the vias is preferred before the optics are applied.

BRIEF DESCRIPTION OF THE DRAWINGS

In the following, a sensor module described here and a method described here are explained in more detail with reference to the drawing using exemplary embodiments. Same reference signs indicate the same elements in the individual figures. However, there are no references to scale shown, rather individual elements may be exaggeratedly large for a better understanding.

In the Figures:

FIGS. 4 to 8A-8B show schematic sectional views of exemplary embodiments of optical embodiment for optoelectronic sensor modules;

DETAILED DESCRIPTION OF ILLUSTRATIVE EMBODIMENTS

Figure 1A:
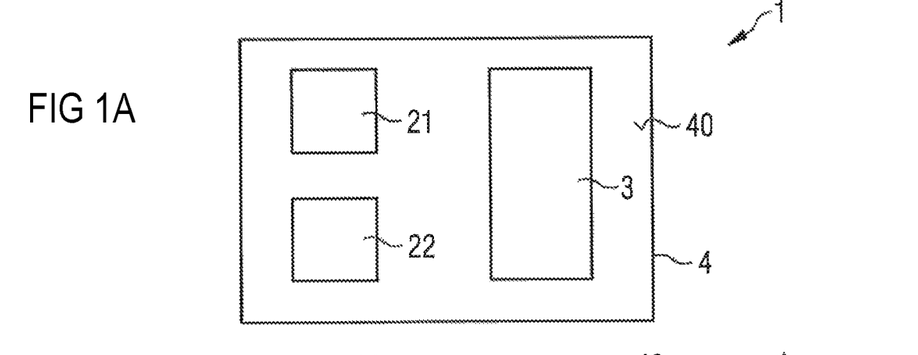
FIGS. 1A-1B, 2A-2B, 3A-3B, 12A-12B and 13A-13B each show a schematic top view and a schematic sectional view of exemplary embodiments of optoelectronic sensor modules.
Figure 1B:
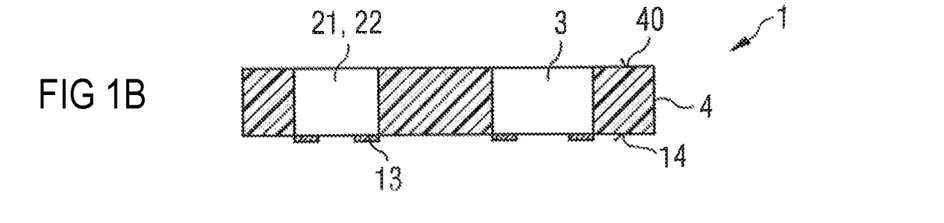

In FIG. 1 an exemplary embodiment of an optoelectronic sensor module 1 is illustrated, see the top view in FIG. 1A and the sectional view in FIG. 1B.

The sensor module 1 comprises a first semiconductor transmitter chip 21 and a second semiconductor transmitter chip 22. The two semiconductor transmitter chips 21 and 22 are designed to generate radiation of different wavelengths. There is also a semiconductor detector chip 3 for detecting the radiation emitted by the semiconductor transmitter chips 21, 22 which is reflected at or in an object not shown in FIG. 1.

The chips 21, 22, 3 are mechanically fixed in a potting body 4 in a common plane, the potting body being opaque to the respective radiation. The potting body 4, for example, is made of a black epoxy. The main surfaces of the chips 21, 22, 3 for emission and detection of the radiation are located on a common detection side 40. Thus the detection side 40 is formed by the potting body 4 together with the chips 21, 22, 3.

The chips, 21, 22, 3 are each flip chips, so that electrical contact surfaces 13 for electrical contacting of sensor module 1 are located on a mounting side 14 opposite the detection side 40. The semiconductor detector chip 3, for example, is a single-channel photodiode, the semiconductor transmitter chips 21, 22 are formed by LED chips.

Figure 2A:
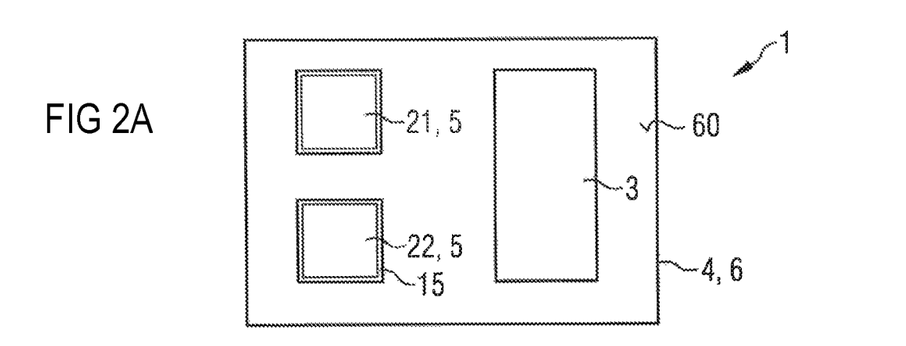
Figure 2B:
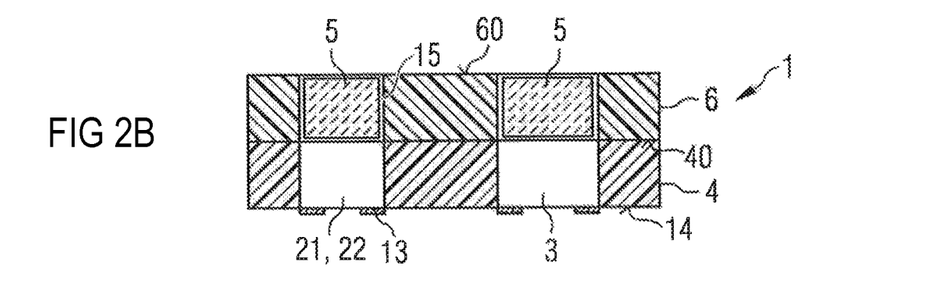

Sensor module 1, as illustrated in conjunction with FIG. 2, additionally has several optics 5. Optics 5 are preferably each designed as multiple lens field. Each of the chips 21, 22, 3 is assigned exactly one of the optics 5. The optics 5 are firmly integrated in a further potting body 6, which is opaque to the radiations.

The further potting body 6 has a light exit surface 60 facing away from the potting body 4, in which the surfaces of the optics 5 facing away from the chips 21, 22, 3 also lie or approximately lie. Side surfaces of the optics 5, as well as side surfaces of the chips 21, 22, 3, are completely covered by the further potting body 6 and the potting body 4.

As in all other embodiment examples, it is possible that the optics 5 are surrounded on all sides roundabout by a reflector body 15 on all side surfaces. The reflector body 15, for example, is a reflective encapsulation, such as an epoxy, to which reflective particles such as titanium dioxide are added. Deviating from the illustration in FIG. 2, such a reflector body 15 may also be present at the optics 5 of the semiconductor detector chip 3. Furthermore, it is possible that such reflector bodies 15 are attached to the side surfaces of the semiconductor transmitter chips 21, 22. The same can apply to all other exemplary embodiments.

For the rest, the exemplary embodiment of FIG. 2 corresponds to that of FIG. 1.

Figure 3A:
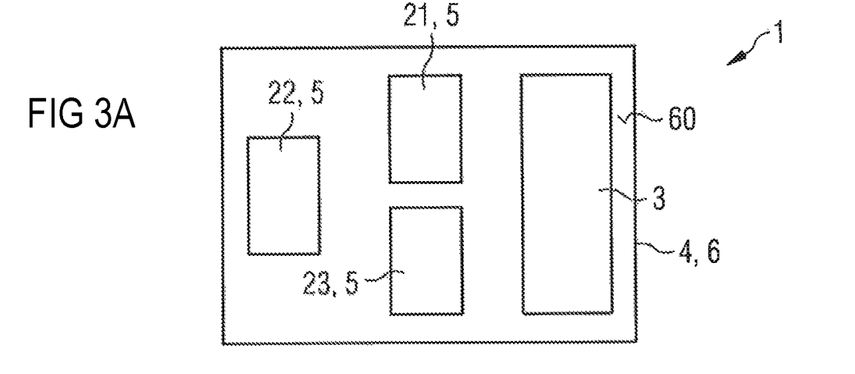
Figure 3B:
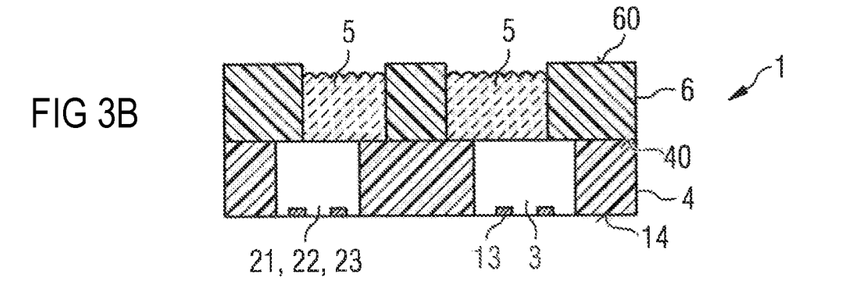

In FIG. 3 is shown that three semiconductor transmitter chips 21, 22, 23 are available for emitting radiations of different wavelengths. The semiconductor transmitter chips 21, 22, 23 are arranged in a triangle. Deviating from this, a linear arrangement of the semiconductor transmitter chips 21, 22, 23 is also possible.

The optics 5 can be mounted eccentrically on the chips 21, 22, 23, 3. This allows the main emission and main reception directions of the chips 21, 22, 23, 3 to be set by means of optics 5. Deviating from FIG. 3, such changes in the main directions of emission and main directions of reception may also be effected by optics 5 which are arranged congruently or approximately congruently on chips 21, 22, 23, 3 as illustrated in conjunction with FIG. 2.

As in all other exemplary embodiments, it is possible that the contact surfaces 13 do not project beyond the potting body 4, but are flush with the mounting side 14.

Figure 4:
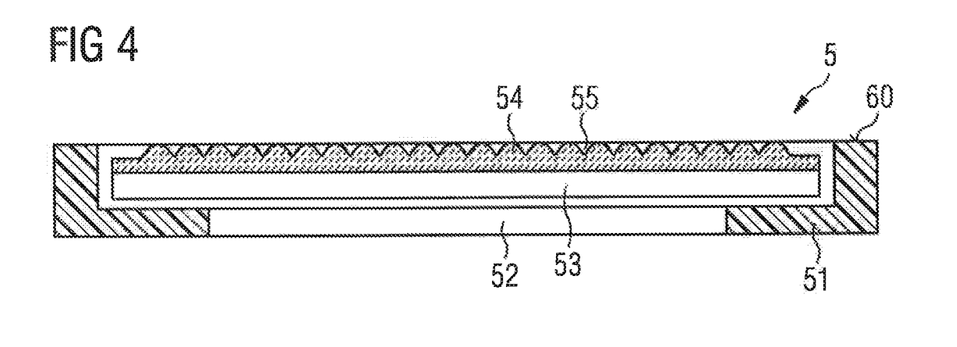

In FIG. 4 an exemplary embodiment for an optics 5 is shown, which can be used in all exemplary embodiments of the sensor module 1. Optics 5 has an entrance window 52 which may have or may be an anti-reflection coating. The entrance window 52 is followed by an optional base layer 53, on which a lens array 54 is located. The base layer 53 and the lens array 54 may have different refractive indices.

Optionally, a frame 51 is provided for mechanical stabilization and to avoid scattered radiation or optical crosstalk, which is preferably opaque to the radiations involved. In addition, a protective layer 55 is preferred, which extends in particular over the light exit surface 60. To prevent the penetration of moisture or other contaminants, the protective layer 55 can extend on the side surfaces of the base layer 53 and the lens array 54 and/or up to the entrance window 52. The protective layer 55 can also be designed as an anti-reflective layer.

Figure 5:
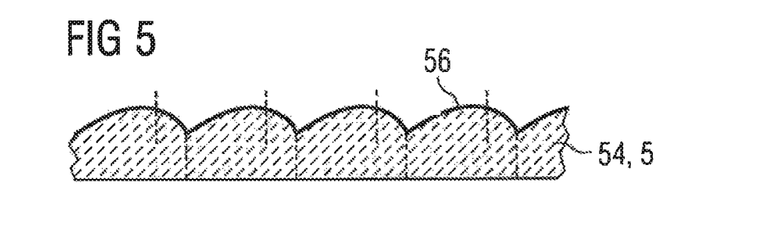

FIG. 5 illustrates the lens array 54 of an exemplary optics 5. The lens array 54 can be used in optics 5 of FIG. 4, for instance.

The lens array 54 is composed of a large number of lens elements 56. Unlike FIG. 4, the lens elements 56 of FIG. 5 are asymmetrically shaped so that an optical axis is obliquely oriented. An area of maximum thickness of the lens elements 56 is thus arranged eccentrically, relative to the respective lens element 56.

Figure 6:
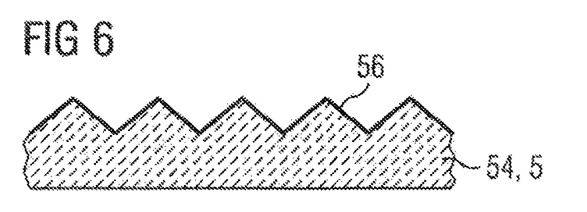
Figure 7:
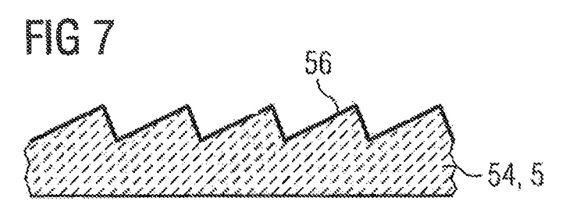

In contrast, according to FIG. 6, the lens elements 56 are formed by symmetrical prisms. FIG. 7 illustrates that the lens elements 56 can also be formed by asymmetrical prisms when viewed in cross-section.

Figure 8A:
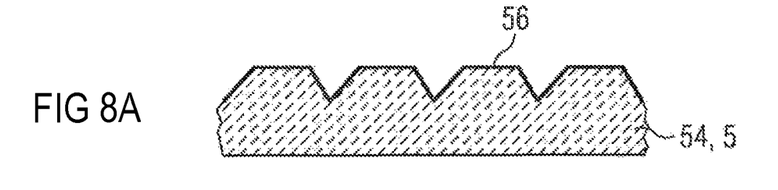
Figure 8B:
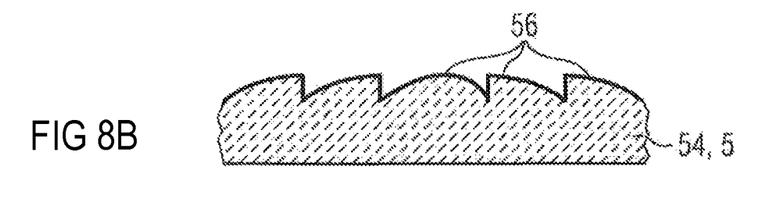

According to FIG. 8A, the lens elements 56 are realized by truncated pyramids or truncated cones. FIG. 8B illustrates that the rings or stripes of a Fresnel lens, for example, can also be used as lens elements.

In FIG. 9 schematic top views are shown. Each of the top views can use lens arrays 54 and lens elements 56, as shown in conjunction with FIGS. 4 through 8.

Figure 9A:
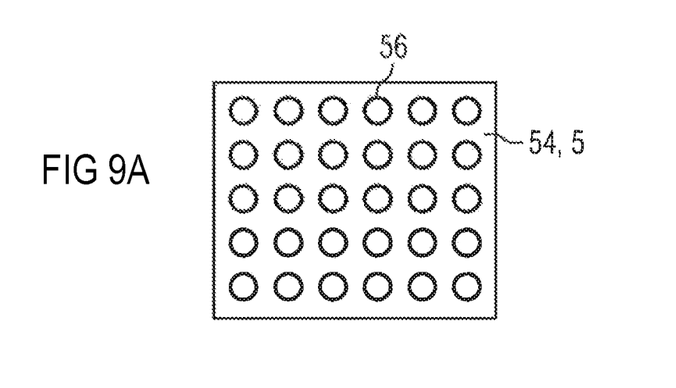
FIGS. 9A-9C show schematic top views of exemplary embodiments of optics for optoelectronic sensor modules.

According to FIG. 9A, the round lens elements 56 are regularly arranged in a rectangular pattern. A hexagonal arrangement pattern can also be used instead of a rectangular one. The lens elements 56 essentially fill the lens array 54 completely. Seen from above, the lens array 54 has a square or rectangular outline.

Figure 9B:
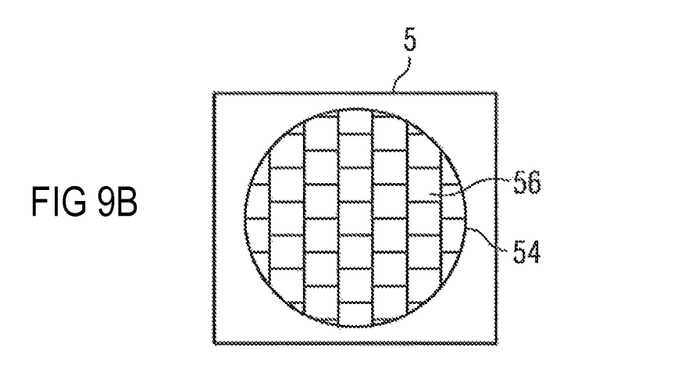

According to FIG. 9B, the lens elements 56 are square or rectangular when viewed from above. The lens array 54 as a whole is circular in shape, seen from above. The optics 5 itself can have a square or rectangular ground plan or, in deviation from the drawing, be congruent with the lens array 54.

Figure 9C:
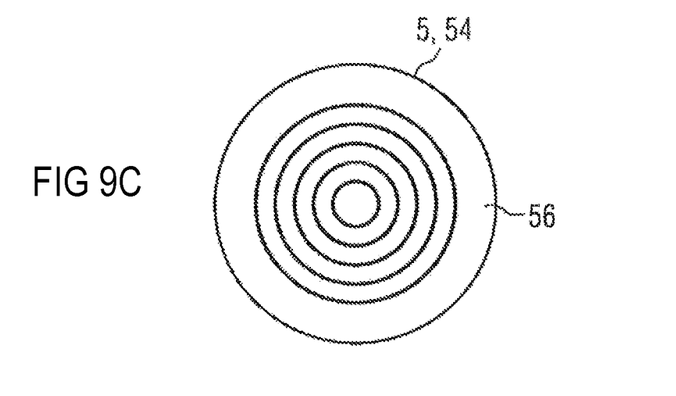

According to FIG. 9C, the lens elements 56 are of a circular shape, for example, for a Fresnel lens.

FIG. 10 illustrates a method for the production for sensor module 1. According to FIG. 10A, the chips 21, 22, 23, 3 are provided. All electrical contact surfaces 13 can point in the same direction.

Figure 10A:
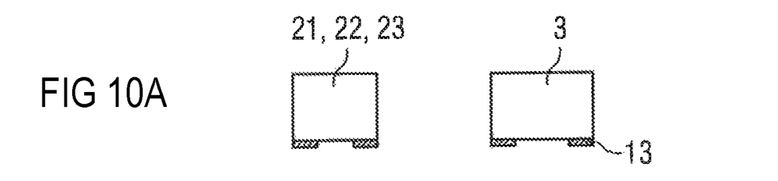
FIGS. 10A-10D, 11A-11B and 14A-14D show schematic cross-sections of process steps for producing optoelectronic sensor modules.
Figure 10B:
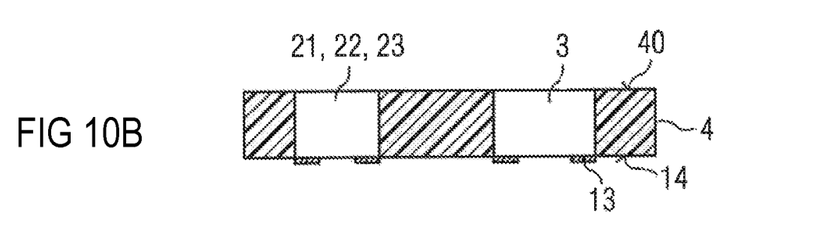

FIG. 10B illustrates that the potting body 4 is created. The electrical contact surfaces 13 are preferably protected by a non-drawn foil when producing the potting body 4 and can project above the potting body 4.

Figure 10C:
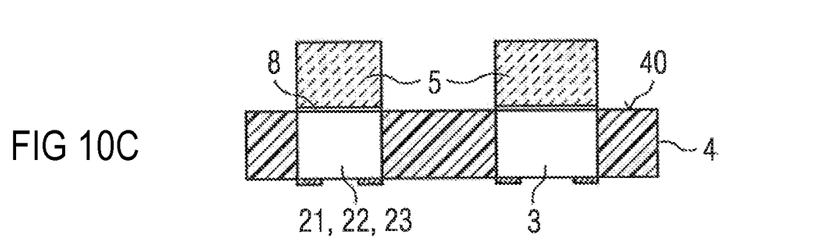

In the process step according to FIG. 10C, the optics 5 are attached to the chips 21, 22, 23, 3 via locally applied adhesive layers 8.

Subsequently, see FIG. 10D, the further potting body 6 is produced directly at the optics 5 and directly at the potting body 4.

Figure 10D:
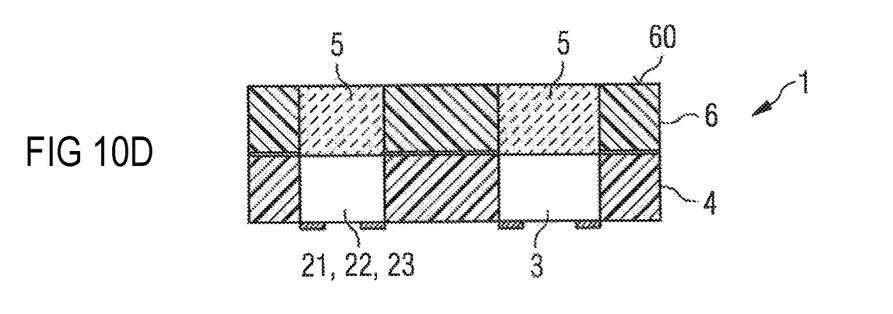
Figure 11A:
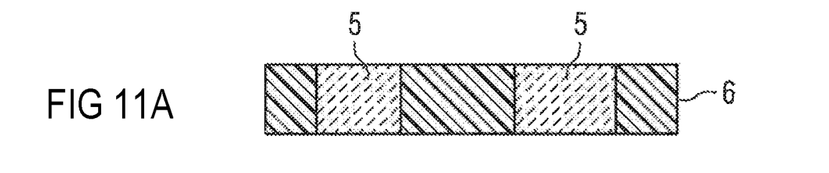
Figure 11B:
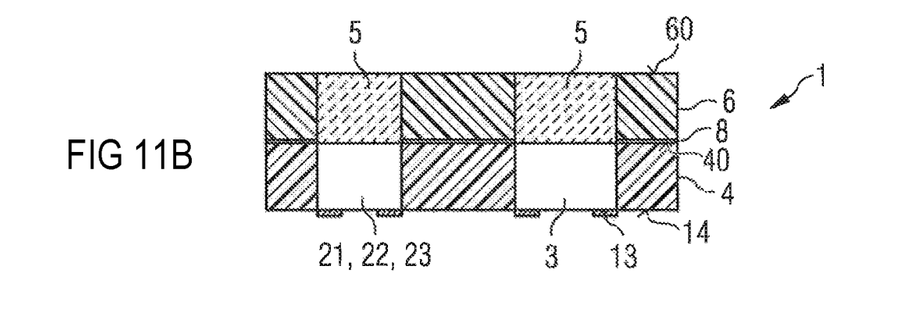

FIGS. 11A and 11B illustrate alternative process steps to FIGS. 10C and 10D. According to FIG. 11A, the further potting body 6 is formed around the optics 5 before the optics 5 are attached to the chips 21, 22, 23, 3. The finished further potting body 6 with the optics 5 is then attached to the potting body 4 with the chips 21, 22, 23, 3 via an adhesive layer 8, for example.

Figure 12A:
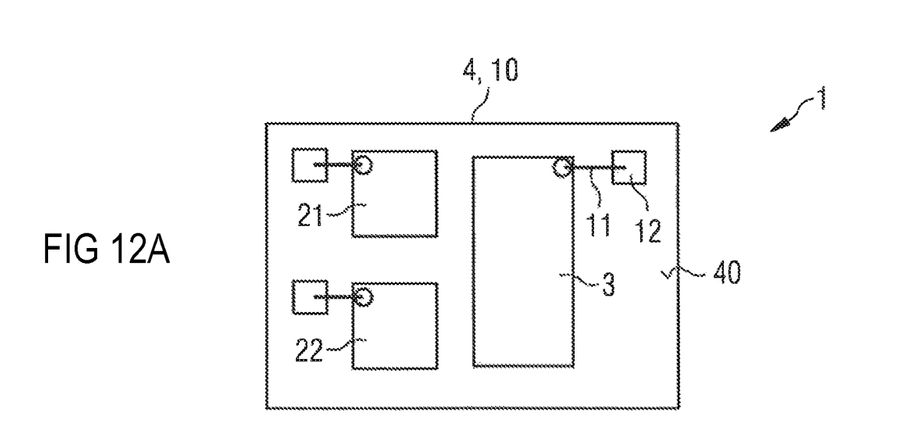
Figure 12B:
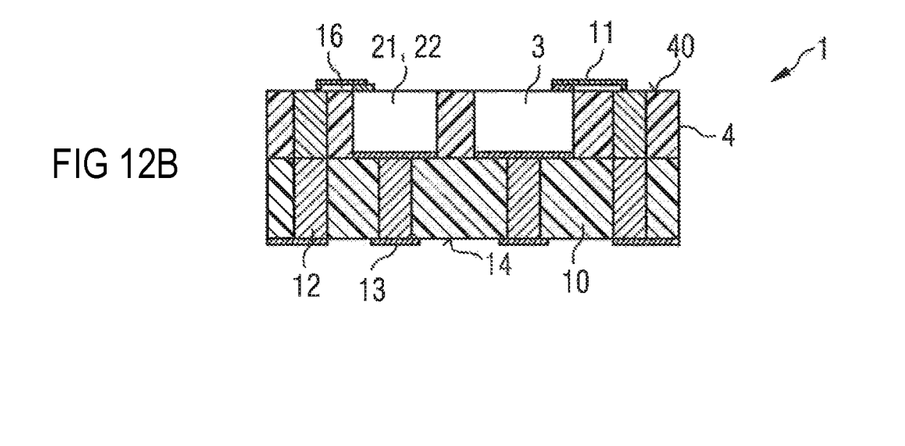

In the exemplary embodiment shown in FIG. 12, there are several conductor tracks 11 on the detection side 40 of the potting body 4 for electrical contacting of the chips 21, 22, 3. The conductor tracks 11 are attached to vias 12. The vias 12 are located on the side next to the chips 21, 22, 3, preferably at an edge area of the potting body 4, so that an area between the chips 21, 22, 3 is free of the vias 12.

Optionally, electrical insulations 16 are provided on the detection side 40, which extend across a boundary between the side surfaces of the chips 21, 22, 3 and the potting body 4. By means of such insulations 16 a material of the conductor tracks 11 may be prevented from reaching the side surfaces of the chips 21, 22, 3. The chips 21, 22, 3 are not designed as flip chips, so that electrical contact is made on opposite main sides of the chips 21, 22, 3.

The potting body 4 is attached to an optional carrier 10. The vias 12 penetrate both the potting body 4 and the carrier 10. If the carrier 10 is present, the mounting side 14 is formed by the carrier and the contact surfaces 13 are located on the carrier 10. If the carrier 10 is omitted, the contact surfaces 13 are formed on the chips 21, 22, 3 and on the potting body 4 in the area of the vias 12.

Figure 13A:
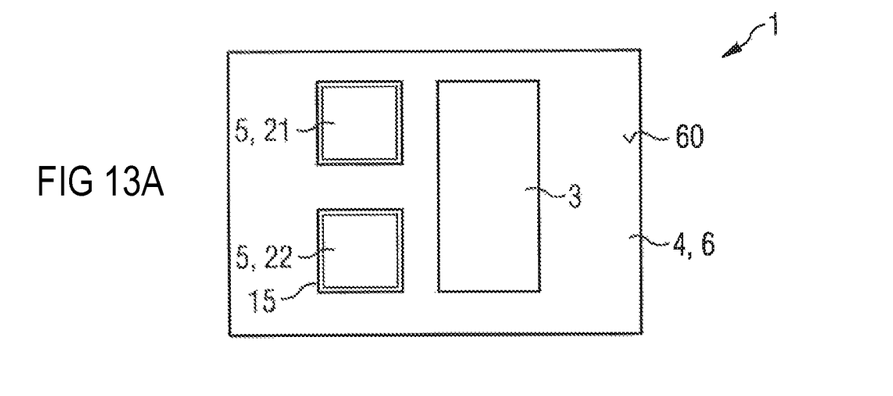
Figure 13B:
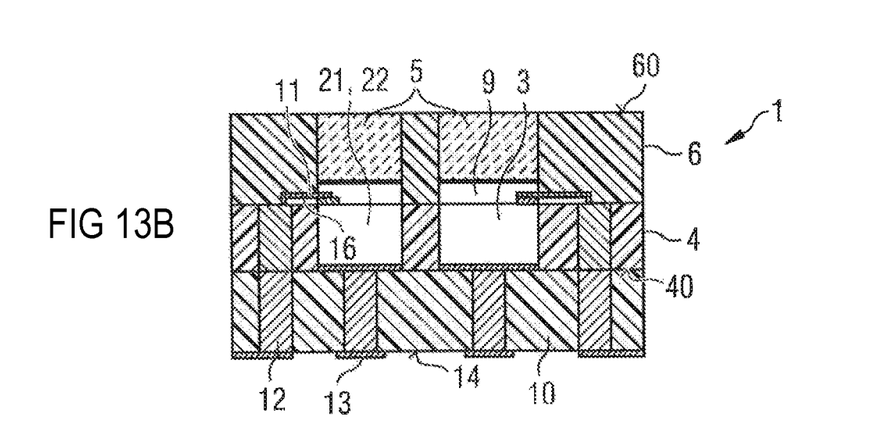

In the exemplary embodiment of FIG. 13, the optics 5 are also present. Between the optics 5 and the chips 21, 22, 3 there is a transparent intermediate layer 9, which can protrude in the direction away from the carrier 10 over the conductor tracks 11.

For the rest, the explanations on FIG. 12 also apply to FIG. 13. Furthermore, more semiconductor transmitter chips 21, 22, 23 may be present than drawn and the optics 5 may be applied off-center, see FIG. 3.

FIG. 14 illustrates a production method in particular for the sensor module 1 of FIG. 13. According to FIG. 14A the chips 21, 22, 3 are applied to the carrier 10. Then the potting body 4 is produced. The optional insulations 16 are then applied and the conductor tracks 11 are created. Finally, the transparent intermediate layer 9 is formed throughout.

Figure 14A:
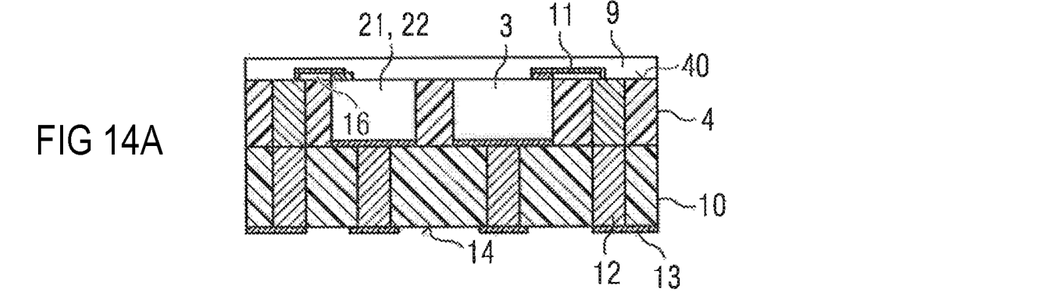
Figure 14B:
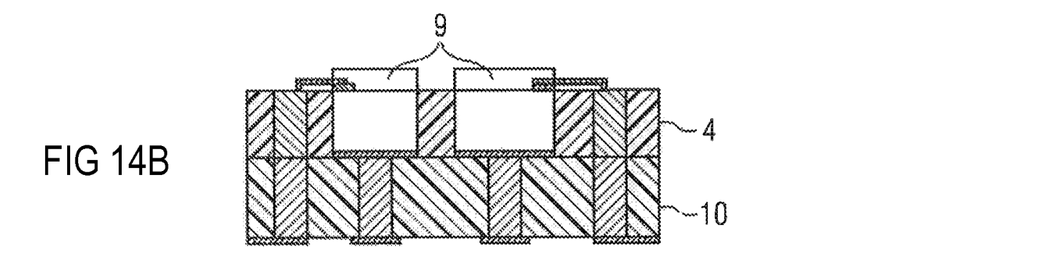

Then, see FIG. 14B, the intermediate layer 9 is partially removed and thus structured, so that the intermediate layer 9 essentially only remains above the chips 21, 22, 3.

Figure 14C:
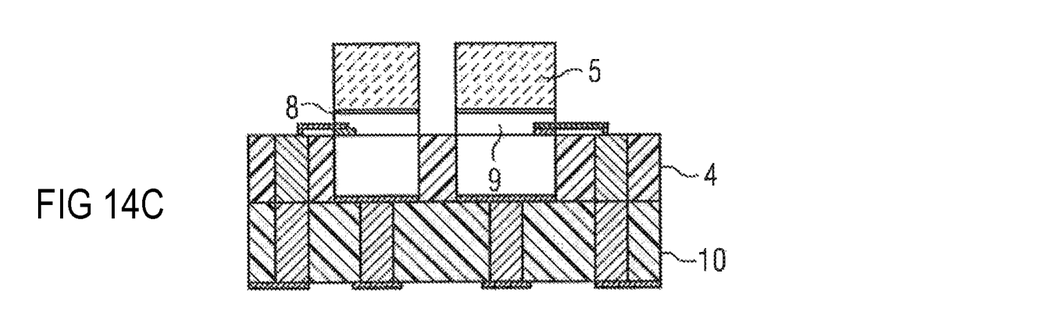

Subsequently, see FIG. 14C, the optics 5 are applied. An adhesive layer 8 can be used or the optics 5 adhere directly to the intermediate layer 9.

Figure 14D:
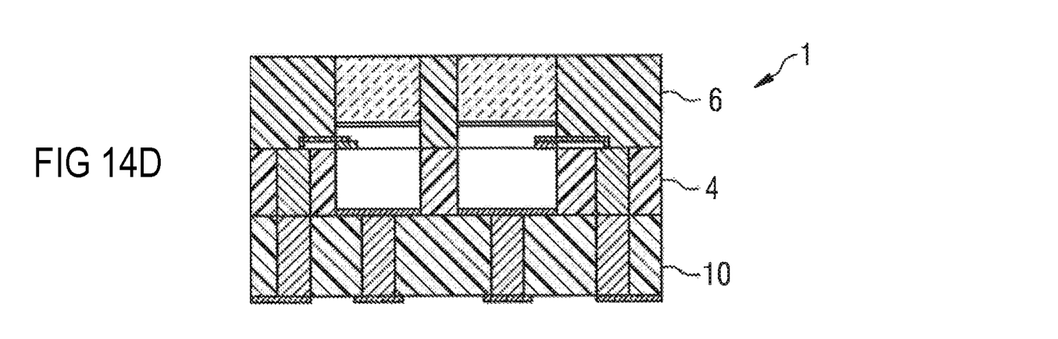

Finally, see FIG. 14D, the further potting body 6 is created.

Optionally, the carrier 10 can be removed in a non-drawn, further process step, or the carrier 10 remains in the finished sensor modules 1.

Figure 15A:
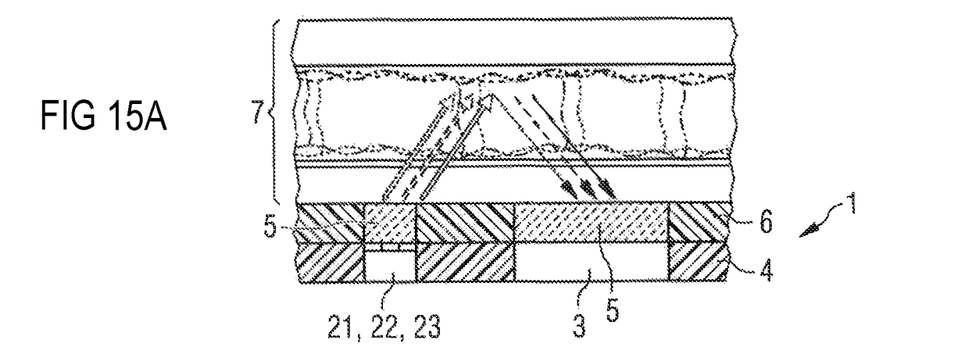
FIGS. 15A-15B show schematic diagrams of the functional principle of the optoelectronic sensor modules.

FIG. 15 explains the functional principle of sensor module 1 in its application as a pulse oximeter. Sensor module 1 is located directly on a body part 7, for example, a wrist or a finger. Radiations of different wavelengths from the semiconductor transmitter chips 21, 22, 23 are irradiated into the body part 7, reflected there and detected via the semiconductor detector chip 3. The various radiations are directed via optics 5 into the desired direction. The first semiconductor transmitter chip 21 emits preferably at 940 nm, the second semiconductor transmitter chip 22 at 660 nm and the third semiconductor transmitter chip 23 at 535 nm.

Figure 15B:
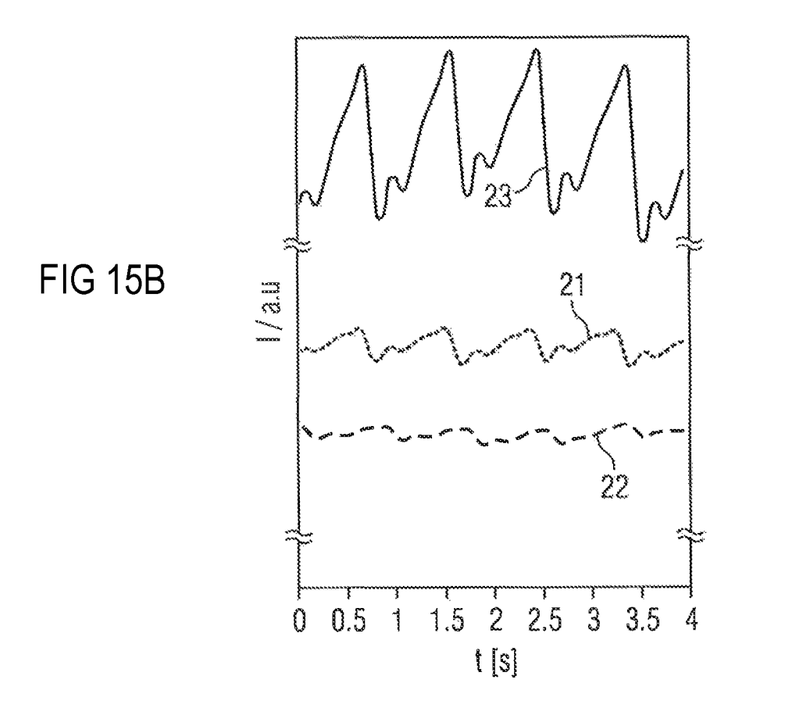

As shown in FIG. 15B, the course of a photocurrent I in relation to the time t of the three different radiations is measured. The pulse frequency in particular is determined from the signal originating from the third semiconductor transmitter chip 23. The oxygen saturation is determined from the signals of the radiation of the first and second wavelengths of the first and second semiconductor transmitter chips 21, 22.

The measurement principle of sensor module 1 based on the three different wavelengths is also described, for example, in the publication Health Monitoring and Fitness Tracking by OSRAM Opto Semiconductors from 2016. The disclosure content of this publication is incorporated by reference.

Unless otherwise indicated, the components shown in the figures follow each other directly in the order indicated. Layers not touching each other in the figures are spaced from each other. As far as lines are drawn parallel to each other, corresponding surfaces are also parallel to each other. Also, unless otherwise indicated, the relative positions of the drawn components to each other are correctly reproduced in the figures.

The invention is not restricted to the exemplary embodiments by the description on the basis of said exemplary embodiments. Rather, the invention encompasses any new feature and also any combination of features, which in particular comprises any combination of features in the patent claims and any combination of features in the exemplary embodiments, even if this feature or this combination itself is not explicitly specified in the patent claims or exemplary embodiments.

The invention claimed is:

1. An optoelectronic sensor module comprising:
a first semiconductor transmitter chip configured to emit radiation of a first wavelength;
a plurality of optics;
a second semiconductor transmitter chip configured to emit radiation of a second wavelength different from the first wavelength;
a semiconductor detector chip configured to detect the radiation of the first and second wavelengths; and
a first potting body being opaque to the radiation of the first and second wavelengths, the first potting body directly covering side surfaces of the chips and mechanically connecting the chips located in a common plane to one another,
wherein a distance between the chips is less than or equal to twice an average diagonal length of the chips,
wherein each optics is in a one-to-one correspondence with one of the chips and at least one of the optics comprises a multiple lens array,
wherein each side surface of the optics is directly covered by a second potting body being opaque to the radiations,
wherein at least one of the optics has an optical axis oriented obliquely to an associated chip, and
wherein the sensor module is adapted to rest against a body part to be examined.

2. The optoelectronic sensor module according to claim 1, wherein a distance between the chips and a light exit surface of an associated optics is at most 50% of a mean diagonal length of the chips.

3. The optoelectronic sensor module according to claim 1, further comprising:
a third semiconductor transmitter chip configured to emit radiation of a third wavelength different from the first and second wavelengths,
wherein the semiconductor detector chip is also configured to detect the radiation of the third wavelength,
wherein the first potting body is opaque to the radiation of the third wavelength, and
wherein the distance between the chips is less than or equal to half a mean diagonal length of the chips.

4. The optoelectronic sensor module according to claim 3, wherein the first wavelength is 940 nm, the second wavelength is 660 nm and the third wavelength is 535 nm, each with a tolerance of not more than 10 nm, and wherein the sensor module is configured for pulse oximetry.

5. A method for producing an optoelectronic sensor module comprising a first semiconductor transmitter chip configured to emit radiation of a first wavelength, a second semiconductor transmitter chip configured to emit radiation of a second wavelength different from the first wavelength, a semiconductor detector chip configured to detect the radiation of the first and second wavelengths, and a potting body, which is opaque to the radiation of the first and second wavelengths, and which directly covers side surfaces of the chips and mechanically connects the chips located in a common plane to one another, wherein a distance between the chips is less than or equal to twice an average diagonal length of the chips and wherein the sensor module is adapted to rest against a body part to be examined, the method comprising:
providing the chips;
encapsulating the chips so that the potting body is formed; and
applying optics to the potting body including the chips,
wherein the optics are glued onto the potting body before forming a further potting body,
wherein each side surface of the optics is directly and completely covered by a material of the further potting body when the further potting body is formed,
wherein each optics is in a one-to-one correspondence with one of the chips, and
wherein at least one of the optics is formed by a multiple lens array.

6. The method according to claim 5, wherein the further potting body is formed directly onto a main side of the potting body.

7. The method according to claim 5, further comprising:
producing electrical conductor tracks on a detection side of the potting body, which is opposite to a mounting side of the sensor module, before applying the optics; and
covering the entire detection side including the conductor tracks with a continuous transparent intermediate layer after producing the conductor tracks.

8. The method according to claim 7, wherein the intermediate layer is structured so that the conductor tracks are partially or completely exposed.

9. The method according to claim 8, wherein the optics are applied to regions of the intermediate layer that remain after structuring, and wherein the further potting body is subsequently formed.

10. The method according to claim 5,
wherein the potting body with the integrated chips is applied on a carrier,
wherein all electrical contact surfaces of the sensor module are located on a side of the carrier facing away from the chips, and
wherein the sensor module is surface mountable.

11. The method according to claim 10,
wherein electrical conductor tracks are produced before the optics are applied,
wherein the electrical conductor tracks are produced on a detection side of the potting body, which is opposite a mounting side of the sensor module,
wherein, after producing the conductor tracks, the entire detection side including the conductor tracks is covered with a continuous transparent intermediate layer,
wherein the conductor tracks are electrically connected to vias before the optics are applied, and
wherein the vias completely pass through the potting body and the carrier in a direction perpendicular to the detection side.

12. A method for producing an optoelectronic sensor module comprising a first semiconductor transmitter chip configured to emit radiation of a first wavelength, a second semiconductor transmitter chip configured to emit radiation of a second wavelength different from the first wavelength, a semiconductor detector chip configured to detect the radiation of the first and second wavelengths, and a potting body, which is opaque to the radiation of the first and second wavelengths, and which directly covers side surfaces of the chips and mechanically connects the chips located in a common plane to one another, wherein a distance between the chips is less than or equal to twice an average diagonal length of the chips and wherein the sensor module is adapted to rest against a body part to be examined, the method comprising:
providing the chips;
encapsulating the chips so that the potting body is formed; and
forming a further potting body so that each lateral surface of optics is directly and completely covered by a material of the further potting body,
wherein the further potting body with the integrated optics is glued onto the potting body over an entire surface,
wherein each optics is in a one-to-one correspondence with one of the chips, and
wherein at least one of the optics is formed by a multiple lens array.

13. The method according to claim 12, further comprising:
producing electrical conductor tracks on a detection side of the potting body, which is opposite to a mounting side of the sensor module, before the further potting body with the optics; and
covering the entire detection side including the conductor tracks with a continuous transparent intermediate layer after producing the conductor tracks.

14. The method according to claim 13, wherein the intermediate layer is structured so that the conductor tracks are partially or completely exposed.

15. The method according to claim 14, wherein the optics are applied to regions of the intermediate layer that remain after structuring.

16. The method according to claim 12,
wherein the potting body with the integrated chips is applied on a carrier,
wherein all electrical contact surfaces of the sensor module are located on a side of the carrier facing away from the chips, and
wherein the sensor module is surface mountable.

17. The method according to claim 16,
wherein electrical conductor tracks are produced before the further potting body with the optics is applied,
wherein the electrical conductor tracks are produced on a detection side of the potting body, which is opposite a mounting side of the sensor module,
wherein, after producing the conductor tracks, the entire detection side including the conductor tracks is covered with a continuous transparent intermediate layer,
wherein the conductor tracks are electrically connected to vias before the further potting body with the optics is applied, and
wherein the vias completely pass through the potting body and the carrier in a direction perpendicular to the detection side.

* * * * *